United States Patent

Pritz et al.

[11] 3,945,379
[45] Mar. 23, 1976

[54] INJECTION DEVICE

[75] Inventors: Howard B. Pritz; Sherwood G. Talbert, both of Columbus, Ohio

[73] Assignee: SmithKline Corporation, Philadelphia, Pa.

[22] Filed: Aug. 8, 1974

[21] Appl. No.: 495,625

[52] U.S. Cl. ............................................. 128/173 H
[51] Int. Cl.[2] ............................................. A61M 5/30
[58] Field of Search ............ 128/173 H, 216, 218 R, 128/218 F, 218 A; 222/389, 327; 239/322

[56] References Cited
UNITED STATES PATENTS

| | | | |
|---|---|---|---|
| 2,605,763 | 8/1952 | Smoot | 128/173 H |
| 2,653,602 | 9/1953 | Smoot | 128/173 H |
| 3,515,130 | 6/1970 | Tsujino | 128/173 H |
| 3,561,443 | 2/1971 | Banker | 128/173 H |
| 3,752,368 | 8/1973 | Robertson | 222/389 X |

FOREIGN PATENTS OR APPLICATIONS

| | | | |
|---|---|---|---|
| 971,162 | 9/1964 | United Kingdom | 128/173 H |

Primary Examiner—Robert W. Michell
Assistant Examiner—Lee S. Cohen
Attorney, Agent, or Firm—Smith, Harding, Earley & Follmer

[57] ABSTRACT

A pressure operated injection device supports an ampul containing a plunger. A ram which actuates the plunger is spring biased to a retracted position and is advanced by a gas under pressure. A source of gas under pressure is connected by a passage to a gas accumulating chamber which in turn is connected by a passage to the ram with a valve being provided in each passage. The valves admit gas to the ram from the accumulating chamber at a predetermined pressure and simultaneously prevent the admission of any further gas from the source of gas and, at a substantially lower pressure, close the passage connecting the accumulating chamber and the ram. The device is constructed to exhaust gas to the atmosphere from the ram as it retracts and a manually controlled valve controlling the flow of gas from the source to control the operation of the device.

9 Claims, 10 Drawing Figures

INJECTION DEVICE

BACKGROUND OF THE INVENTION

Devices for injecting medication beneath the skin without the use of a needle by forcing the medication through the epidermis in a high pressure jet are well known to the art. For this purpose it is known to the art to employ an ampul which contains a plunger to force the liquid from the ampul. The prior art devices have a ram for advancing the plunger. Such rams are either spring or gas actuated. Prior art patents are U.S. Pat. Nos. 3,292,622; 3,688,765 and 3,292,621. As against the devices having a spring actuated ram, the devices with a gas actuated ram greatly facilitate providing a convenient design since it eliminates the inflexibility of having to place a powerful compression spring in line with the ram. The most successful gas actuated devices have suffered from being erratic in the injection force generated due to the variation in gas pressure arising from temperature changes arising, for example, from the use of a liquified gas which exerts a cooling effect on vaporizing. Difficulty has been encountered incident to the use of a mechanical system to hold the ram and release it at a predetermined pressure. In addition, gas is readily wasted thus reducing the number of shots possible from the gas source when a gas cartridge is employed. The injection device of this invention solves these problems.

BRIEF SUMMARY OF THE INVENTION

A pressure operated injection device has a housing for the support of an ampul having a plunger. The plunger is actuated by a gas operated ram which is biased to a retracted position. A source of gas under pressure is provided to supply a chamber for accumulating gas. A manually operated on/off valve controls the flow of gas from said source. Pressure operated means admits gas to the ram from the accumulating chamber and simultaneously stops the flow of gas to the accumulating chamber from the source of gas when a predetermined pressure is reached in the accumulating chamber.

DETAILED DESCRIPTION

Figure 1:
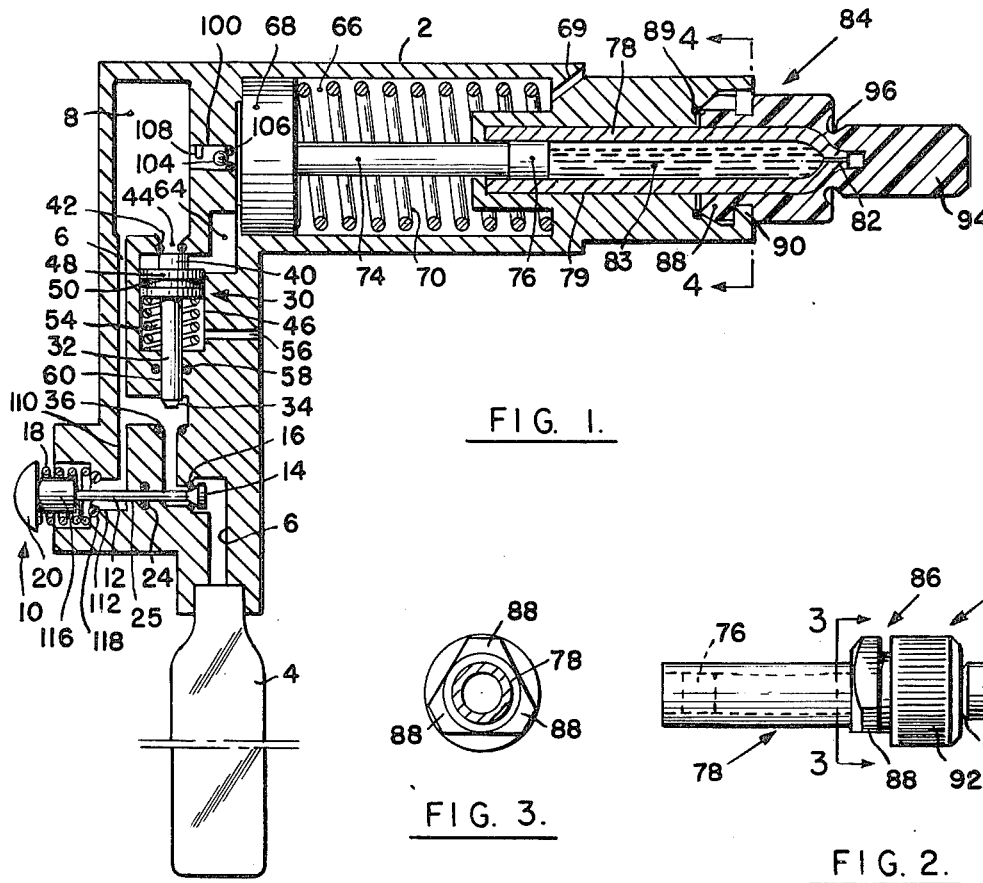
FIG. 1 is a diagrammatic view of a device in accordance with the invention.

Referring to FIG. 1, the injection device of the invention has a housing 2 to which a gas cartridge 4 is removably attached. A passage 6 connects the interior of gas cartridge 4 to a gas accumulating chamber 8. A valve 10 controls the flow of gas through passage 6. Valve 10 has a stem 12 and an enlarged portion 14 which is adapted to seat against an O-ring 16 in passage 6. Portion 14 is urged against O-ring 16 by virtue of a compression coil spring 18 urging valve button 20 outwardly. An O-ring 24 is employed to act as a seal about stem 12 as it passes through bore 25.

The flow of gas through passage 6 is also controlled by a pressure differential operated device 30. Device 30 has a stem 32 which has a lower beveled face 34 adapted to engage O-ring 36 to close off passage 6. It also has a solid cylindrical valve member 40 which is adapted to engage an O-ring 42 to close passage 44 which connects gas accumulation chamber 8 to a cylindrical cavity 46. Valve member 40 is fixedly secured to a piston 48 in cavity 46 which carries a sealing O-ring 50. Piston 48 is spring biased upwardly by a compression coil spring 54. A passage 56 connects the lower portion of cylindrical cavity 46 to the atmosphere to vent air when piston 48 moves downwardly. An O-ring 58 seals about valve stem 32 as it passes through a bore 60 in housing 2.

A passage 64 connects cylindrical cavity 46 to a cylindrical cavity 66 containing a piston 68 to supply gas under pressure behind piston 68. A passage 69 connects cavity 66 to the atmosphere to vent air as the piston 68 advances. Piston 68 is biased in the retracted position by a compression coil spring 70. A rod 74 is connected to piston 68 and together with piston 68 forms a ram engaging a plunger 76 in an ampul 78 of, for example, metal or plastic, seated in a reduced bore 79 and provided with a restricted outlet opening 82. Opening 82 is too small for liquid 83 contained within the ampul to pass through until the pressure is increased during an injection, for example from about .003 inch to about .012 inch in diameter.

Figure 3:
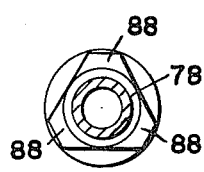
FIG. 3 is a section taken on the plane indicated by the line 3—3 in FIG. 2.

A protective cover 84 overlies a portion of ampul 78 adjacent opening 82 and has an interlocking portion 86 (FIG. 2) with ears 88, 88, 88 (FIG. 3) adapted to removably interlock between O-ring 89 and ears 90, 90, 90 on housing 2. Stop member 91, 91, 91 limit the rotation of ears 88, 88, 88. Cover 84 has an enlarged knurled portion 92 to facilitate rotation and a removable cap portion 94 which can be severed along a weak area indicated at 96 before injection.

A restricted cylindrical passage 100 connects cavity 66 to accumulating chamber 8. Passage 100 is controlled by a ball 104 having a diameter smaller than the diameter of passage 100 and which permits the passage of gas from cavity 66 to chamber 8 and prevents the flow of gas in the reverse direction. Ball 104 seats against O-ring 106 and is retained by a pin 108.

An exhaust passage 110 connects passage 6 to the atmosphere. Passage 110 has an enlarged portion 112 through which valve stem 12 freely passes to permit gases to flow through passage 110 without obstruction by stem 12. Valve 10 has a solid cylindrical member 116 which is adapted to engage an O-ring 118 to close off the enlarged portion 112 of passage 110.

OPERATION

In operation ampul 78 is seated in reduced bore 79 and locked therein by rotating ears 88, 88, 88 behind ears 90, 90, 90. Cap 94 is snapped off at 96. The injection device is placed with the now exposed end of the ampul against the skin of the patient. Valve button 20 is then pushed inwardly to move stem portion 14 away from O-ring 16 and to close the enlarged portion 112 of passage 110 by urging member 116 against O-ring 118. Gas flows through passage 6 into accumulating chamber 8. At a predetermined pressure, the force exerted on valve member 40 overcomes the upward force of spring 54 and valve member 40 is moved away from O-ring 42 moving piston 48 and valve stem 32 downwardly. The movement of valve member 40 clear of O-ring 42 permits the flow of gas into cylindrical cavity 46 and the exertion of pressure against the exposed head of piston 48 which results in the rapid movement of piston 48 and stem 32 downwardly to cause beveled portion 34 to engage O-ring 36 and close passage 6 thus blocking the flow of gas from cartridge 4 to accumulating chamber 8 and preventing any further increase in pressure in chamber 8. Simultaneously, gas passes through passage 64 to a position behind piston 68 causing the movement of rod 74 further into ampul 78 and the consequent movement of plunger 76 to expel the contained liquid 83 through opening 82 in a jet which passes through the epidermis of the patient. As piston 68 advances, air vents through passage 69. During the injection, button 20 must be held down to prevent the exhaustion of gases past valve 10.

Piston 48 remains in the downward position as the gas expands into cavity 66. The valve button 20 having been released to permit valve member 116 to move away from O-ring 118 and member 14 to engage O-ring 16 and block the flow of gas from the cartridge, compression coil spring 70 returns piston 68 and rod 74, gas exhausts from the back of piston 68 through passage 64, passage 44, accumulting chamber 8, passage 6 and passage 110.

As the gas pressure drops to a relatively low figure, spring 54 overcomes the force exerted by the gas on valve member 40 and on piston 48 and urges piston 48 upwardly to force valve member 40 against O-ring 42. At this juncture, piston 68 is still returning to its retracted position and gas is exhausting through opening 100. Ball check valve 104 permits the gas to flow in this direction, while preventing it from flowing in the reverse direction. When the piston 68 and rod 74 reach their original retracted position, the operation is fully completed and the device is ready for the next inoculation as soon as another ampul is inserted.

Obviously the prssure differential operated device 30 can be designed to operate within a wide range. Carbon dioxide is an advantageous gas to employ in the gas cartridge. When this gas is employed, it is advantageous to design the portion of member 40 exposed to pressure when piston 48 is in its uppermost position and spring 54 so that movement of member 40 away from O-ring 42 will occur at a predetermined gas pressure of 500 p.s.i. or higher. 500 p.s.i. is an advantageous pressure since this is the pressure exerted by carbon dioxide at a temperature of approximately 33°F below which it is not anticipated that the temperature of the carbon dioxide would go even if the injection device is operated rapidly. Generally the gas cartridge will contain liquid $CO_2$. The cartridge provides a pressure that varies greatly with a given temperature. To illustrate this sensitivity, the pressure in a carbon dioxide cartridge will be 500 p.s.i. at 33°F and 800 p.s.i. at 70°F. Thus, the operating pressure in the device available from the cartridge will depend on the ambient environment. This variation in pressure with temperature is further accentuated since on vaporizing, carbon dioxide cools the injection device and rapid operation can result in cooling of the device.

Assuming for purposes of illustration a release of the gas from chamber 8 when the gas pressure in chamber 8 reaches 500 p.s.i., it is a simple matter to design piston 68 to provide an initial fluid pressure within the conventional plunger actuated ampul, of the example, about 6,000 p.s.i. with an expansion of, for example, about 2:1 to provide for a drop to about 3,000 p.s.i. at the completion of a one-milliliter injection. Generally speaking, the initial fluid pressure for injection desirably is in the range of from about 5,000 to 8,000 p.s.i. and the final fluid pressure at the end of the injection preferably at a minimum of about 2,000 p.s.i. These ranges will vary depending upon whether the injection is for humans or animals and the nature of the liquid being injected.

Normally the pressure of the $CO_2$ in cartridge 4 will be substantially higher than 500 p.s.i. Thus if the temperature of the $CO_2$ is 80°F, the pressure of the $CO_2$ in cartridge 4 will be 970 p.s.i. Under these circumstances, the pressure is prevented from going above the 500 p.s.i., given by way of example above, due to the fact that at that pressure face 34 of stem 32 has been moved into contact with O-ring 36 to prevent further gas from passing into chamber 8. Thus the injection pressure will be at a predetermined value irrespective of temperature conditions.

The exposed area on the top of piston 48 (i.e., the area not covered by valve member 40) is as large as is convenient in order to keep piston 48 in the down position so that gas can exhaust through passages 64 and 44 as long as possible. For example, the exposed area on the top of the piston may be four times the exposed area on the top of the member 40 so that piston 48 will be returned to its original up position when the original pressure of say 500 p.s.i. has dropped to under 100 p.s.i.

PREFERRED EMBODIMENT

Figures 5, 6, 7, 8, 9:
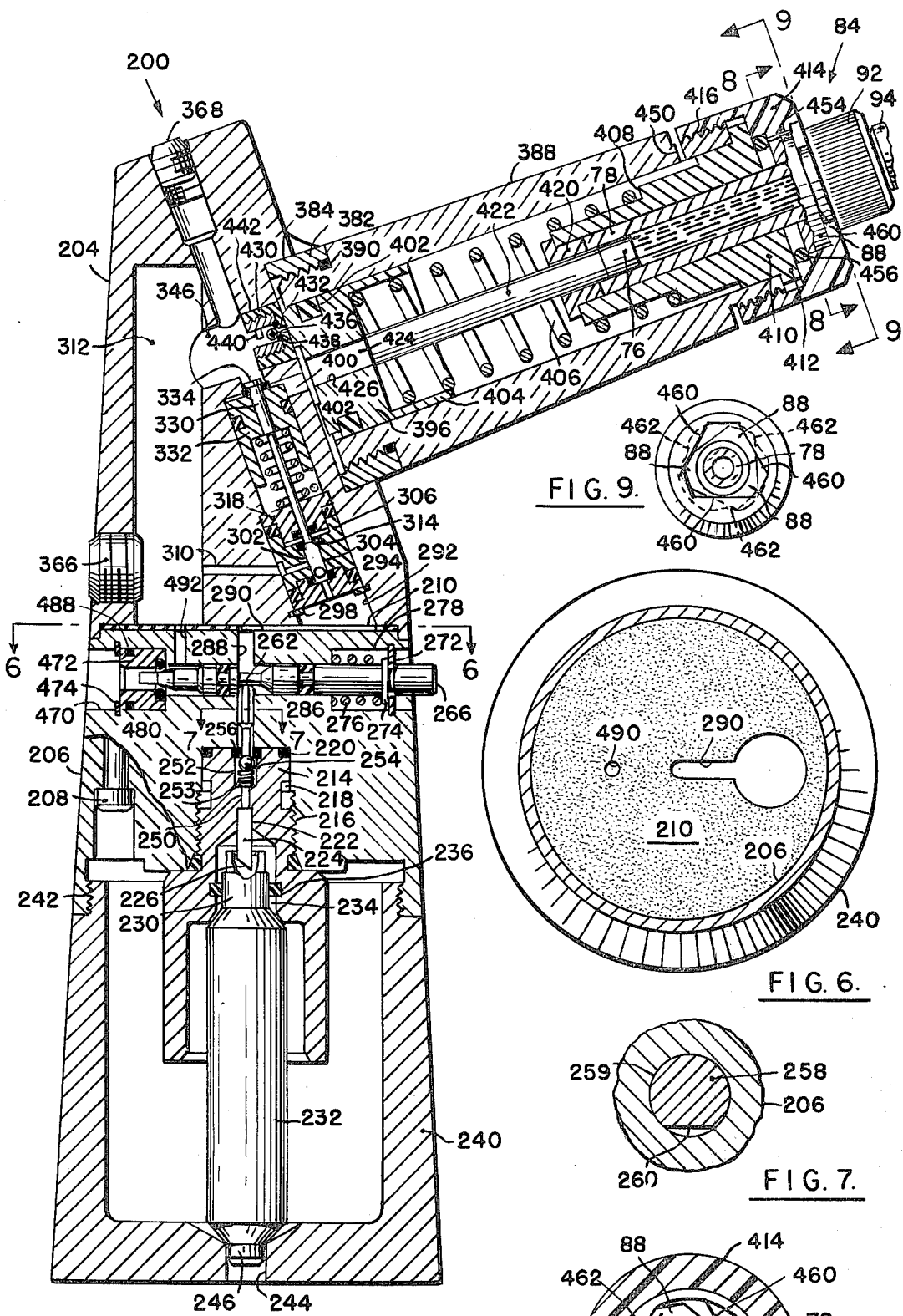
FIG. 5 is a vertical section through a preferred embodiment of the invention.
FIG. 6 is a section taken on the plane indicated by the line 6—6 in FIG. 5.
FIG. 7 is a section taken on the plane indicated by the line 7—7 in FIG. 5.
FIG. 8 is a section taken on the plane indicated by the line 8—8 in FIG. 5.
FIG. 9 is a sectionn taken on the plane indicated by the line 9—9 in FIG. 5.
Figure 10:
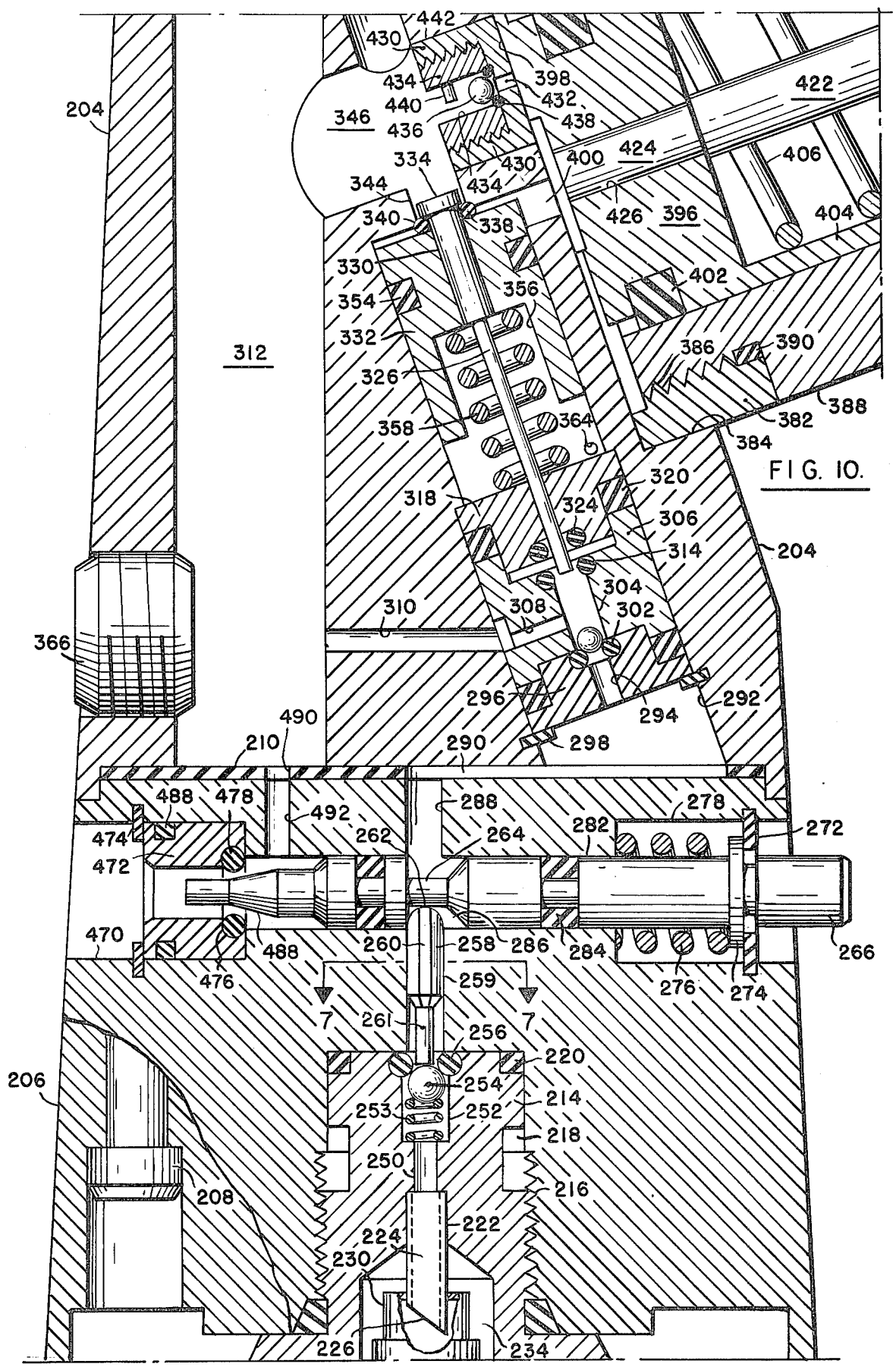
FIG. 10 is an enlarged view of the central portion of the structure shown in FIG. 5.

Injection device 200 shown in FIG. 5 is a preferred embodiment of the invention. Injection device 200 has an upper housing member 204 and a lower housing member 206 which are secured together by machine screws indicated at 208. A seal between housing members 204 and 206 is provided by the gasket 210.

A fitting 214 is threadably secured as indicated at 216 in cavity 218 in lower housing member 206. Fitting 214 carries a gasket 220 which seals between the fitting 214 and lower housing member 206. Fitting 214 has a central bore 222 in which is secured by a pressed fit a hollow needle 224 which has a sharp chamfered lower end 226 to permit entry thereof into the neck 230 of a gas cartridge 232 in a manner well known to the art. Cartridge 232 is accommodated in a recessed portion 234 of fitting 214 and cartridge neck 230 is engaged by O-ring 236. Cartridge 232 is urged upwardly and held in position by a cup-shaped member 240 which is threadably secured at 242 to lower housing member 206 and has an opening 244 to accommodate the lower reduced portion 246 of cartridge 232. Cartridge 232 is the source of gas for the operation of the injection device 200.

Figure 2:
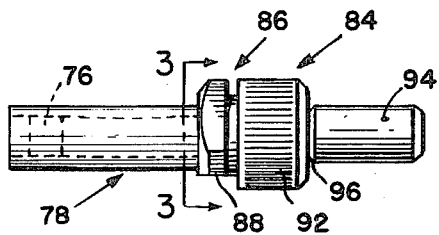
FIG. 2 is a side elevation of the ampul employed in the device of FIG. 1.
Figure 4:
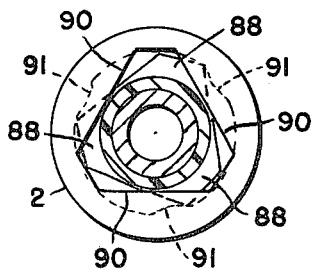
FIG. 4 is a section taken on the plane indicated by the line 4—4 in FIG. 1.

A passage 250 leads upwardly from bore 222 into a circular in cross-section chamber 252 containing a ball 254 having a diameter smaller than the diameter of the chamber 252 and which is normally urged upwardly by a spring 253 against an O-ring 256 to block the upward passage of gas. Above ball 254 is a pin 258 in passage 259 which pin has a flat side 260 and a reduced diameter lower portion 261 to permit the passage of gas past pin 258 in passage 259 and between pin 258 and O-ring 256. The upper end 262 of pin 258 is rounded as shown in FIG. 2 and is adjacent a reduced portion 264 of a spool valve 266.

Spool valve 266 passes freely through the center of a snap ring 272 which is abutted by a ring 274 fixedly secured to spool valve 266. Ring 274 is engaged by a compression coil spring 276 which also engages the inner end of cavity 278 in lower housing member 206 through which spool valve 266 passes. Spool valve 266 also passes through a bore 282 and carries a gasket 284 for sealing engagement with said bore. A conical portion 286 on valve 266 is adapted to engage pin 258 and cam it downwardly to move ball 254 away from O-ring 256 and permit the flow of gas upwardly. The gas flows past ball 254 in chamber 252, past the flat side 260 of pin 258 in passage 259, about reduced portion 264 and into a passage 288 which communicates with an opening 290 in gasket 210 and thence flows upwardly through an opening 292 in upper housing member 204 and through passage 294 in valve seat member 296 retained by a snap ring 298. Valve seat member 296 carries an O-ring 302 against which a ball 304 is adapted to seat.

A second valve seat member 306 has a lateral passage 308 communicating with a passage 310 in upper housing member 204 which in turn communicates with a gas accumulating chamber 312. Valve seat member 306 carries an O-ring 314 which is adapted to be engaged by ball 304 when gas is being supplied to chamber 312.

A bushing 318 carries an O-ring 320 for sealing against upper housing member 204 and O-ring 324 for sealing against valve rod 326. Rod 326 is secured by a pressed fit in opening 330 in piston 332 and has an enlarged cap portion 334 which engages an O-ring 338 which seals against a shoulder 340 at the lower end of a passage 344. Passage 344 communicates with a passage 346 which in turn communicates with gas accumulating chamber 312.

Piston 332 carries a piston sealing ring 354 and has a cavity 356 containing a compression coil spring 358 which bears against bushing 318 and biases piston 332 upwardly. An opening 364 in upper housing member 204 vents air to the atmosphere when piston 332 moves downwardly.

Screw caps 366 and 368 in upper housing member 204 are provided to permit the drilling of passages 310 and 344 respectively and to permit the entry of a rod to move cap portion 334 downwardly to aid disassembly.

A ring member 382 is secured by a pressed fit into a circular opening 384 in upper housing member 204 and has threaded thereto as indicated at 386 a hollow cylindrical member 388. An O-ring 390 provides a seal between ring 382 and member 388. A piston 396 in member 388 has a depending portion 398 which spaces the piston away from upper housing member 204 adjacent passage 400 which connects the portion of opening 292 above piston 332 to the interior of member 388. Packing 402 seals between piston 396 and member 388. Piston 396 has a peripheral flange 404 inside of which is seated a compression coil spring 406. The other end of spring 406 is seated against a shoulder 408 on an ampul support member 410 mounted within member 388 and having a securing flange 412 which lies between the outer end of member 388 and a cap member 414 threaded to member 388 at 416. Ampul support member 410 has secured in its inner end by a pressed fit a bushing member 420 through which rod 422 freely passes. Rod 422 has a reduced end 424 which is secured by a pressed fit into opening 426 in piston 396. Piston 396 and rod 422 form a ram for the advance of the plunger 76 of ampul 78.

A cup member 430 has a small opening 432 having, for example, a diameter of .030 inch communicates with the rear of piston 396 and with a hollow cylindrical member 434 which contains a ball 436 having a diameter smaller than the inner diameter of member 434 and which is adapted to seat on an O-ring 438. A pin 440 depends into chamber 440 to retain ball 436 within the chamber. This entire cup assembly is inserted into an opening 442 in upper housing member 204.

A vent opening 450 provides for a communication between the interior of member 388 and the atmosphere in order to vent air as the piston 396 advances.

Cap member 414 has a shoulder 454 which retains an O-ring 456 against the outer end of ampul support member 410. Similar to the first described embodiment cap 414 is provided with three ears 460 which are adapted to engage ears 88, 88, 88 of an ampul 78. This arrangement forms a bayonet joint for the retention of ampul 78 with ears 88 resting against O-ring 456. Rod 422 enters within ampul 78 and engages ampul plunger 76.

Reverting back to the upper portion of lower housing member 206, bore 282 extends to a cavity 470 in which is secured a valve seat fitting 472 by a split ring 474. Fitting 472 has a recess 476 for support of an O-ring 478. Spool valve 266 has a conical shaped portion 488 which is adapted to engage O-ring 478 when spool valve 266 is advanced to the left as viewed in FIG. 5.

OPERATION

To operate the injection device 200, an ampul 78 is first inserted in ampul support 410 by passing the ears 88 of ampul 78 between the ears 460 of cap 414 and inwardly against O-ring 456. The ampul 84 is then rotated clockwise until ears 88 pass behind the ears 460 on cap 414 to stops 462. The ampul cap 94 is now snapped off and the end of the ampul pressed against the skin of the patient. Spool valve 266 is now moved to the left as viewed in FIG. 5 causing conical portion 286 to move pin 258 downwardly against ball 254 to move the ball away from O-ring 256 and permit the passage of gas from cartridge 232 to pass through hollow needle 222, passage 250, chamber 252, passage 259, passage 288, opening 290 in gasket 210, opening 292, passage 294, the center of member 306, passage 308 and passage 310 into gas accumulating chamber 312. The gas passes through passage 346 and the commencement of passage 344 to cap portion 334. As the gas passes through passage 294, it forces ball 304 upwardly to seal against O-ring 314 to insure that no gas passes into the area of piston 332.

When the pressure in accumulating chamber 312 and above cap portion 334 builds up to a predetermined pressure, for example 500 p.s.i., cap portion 334 and the associated piston 332 and rod 326 are forced downwardly thus clearing cap portion 334 from O-ring 338 and permitting the gas to flow onto the top of piston 332 thus accelerating the downward movement of these elements. Rod 326 engages ball 304 and forces it down against O-ring 302 to prevent the further entry of gas into accumulating chamber 312 and thus limits the operating pressure to the exemplary figure of 500 p.s.i. The gas in accumulating chamber 312 passes through passage 346, passage 344, above piston 332, through passage 400, and into the area behind piston 396. The gas forces piston 396 to advance, which in turn causes the advance of rod 422 and ampul plunger 76 to force the liquid in ampul 78 out through opening 82 under high pressure. The advance of rod 422 and piston 396 is arrested by the engagement of piston 396 with bushing member 420.

On hearing the delivery of the injection which provides a clearly audible sound, the spool valve 266 is released permitting the spring 276 to return spool valve 266 to its original position which permits gas in accumulating chamber 312 to pass downwardly through an opening 490 in gasket 210 through passage 492 in lower housing member 206 and bore 282 and between spool valve 266 and O-ring 478 to the atmosphere. As the gas pressure behind piston 396 drops due to the passage of gas back through passage 400, above piston 332 and through passages 344 and 346 into chamber 312, spring 406 will urge piston 396 back towards its original position. As the pressure continues to drop to, for example, one-fifth of the original triggering pressure in chamber 312, spring 358 forces piston 332 upwardly causing O-ring 338 to bear against shoulder 340 to block the further passage of gas to chamber 312. The residual gas behind piston 396 passes through opening 432 around ball 440 and through member 434 and thence through passage 346 into chamber 312 and thence to the atmosphere.

The expended ampul is then removed by turning the ampul counterclockwise to clear the ampul ears 88 from the ears 460 of cap member 414 and then pulling the ampul outwardly.

The design and operating parameters as discussed with respect to the first embodiment are applicable here and hence need not be discussed again.

It will be understood that the above described embodiments are illustrative and are not intended to be limiting.

We claim:

1. A pressure-operated injection device comprising: a housing,
means to support in the housing an ampul having a plunger and a discharge opening,
a ram slidably mounted in the housing coaxially with the supporting means and adapted to actuate said plunger,
an accumulating chamber in the housing to accumulate gas,
means to supply a gas under prssure to the accumulating chamber,
pressure actuated means responsive to pressure of gas in the accumulating chamber to conduct gas to the ram from the accumulating chamber and stop the supply of gas to the accumulating chamber when the gas pressure in the accumulating chamber reaches a predetermined pressure.

2. A pressure-operated injection device comprising: a housing,
means to support in said housing an ampul having a plunger and a discharge opening,
a ram slidably mounted in the housing coaxially with the supporting means for actuating said plunger,
means to bias the ram to a retracted position,
an accumulating chamber in said housing for accumulating gas,
a source of gas under pressure,
a first passage connecting the chamber and the ram,
a first pressure actuated valve means controlling said first passage,
said first valve means being spring biased to the closed position, opening responsive to a predetermined pressure and remaining open responsive to a pressure ranging from said predetermined pressure to a predetermined lower pressure,
a second passage connecting the accumulating chamber to the source of gas under pressure,
a second valve means controlling said second passage,
means respeonsive to the opening movement of the first valve means to close the second valve means when the first valve means open and prevent further gas from entering the accumulating chamber, and
a manually controlled valve in said second passage upstream of said second valve.

3. A device in accordance with claim 2 in which the source of gas under pressure comprises a container of liquified gas removably secured to the housing.

4. A device in accordance with claim 2 having means to connect the accumulating chamber to the atmosphere during the retraction of the ram.

5. A device in accordance with claim 2 having means to exhaust gas as the ram retracts including a restricted passage connecting the ram and the accumulating chamber, a check valve in the restricted passage preventing flow from the accumulating chamber to the ram and means to connect the accumulating chamber to the atmosphere.

6. A device in accordance with claim 2 in which the means to bias the ram comprises a compression coil spring.

7. A device in accordance with claim 2 having stop means to limit the extension of the ram.

8. A pressure-operated injection device comprising a housing,
means to support in said housing an ampul having a plunger and a discharge opening,
a ram slidably mounted in the housing coaxially with the supporting means for actuating said plunger,
means to bias the ram in a retracted position,
a source of gas under pressure,
said housing having a cylindrical cavity having a top wall, a bottom wall and a side wall, a gas accumulating chamber in the housing, a first passage connecting the chamber with the top of the cavity, a second passage connecting the source of gas with the chamber and third passage connecting the upper portion of the cavity with the ram,
a piston in said cavity having an upper face facing the top of the cavity,
a first valve member controlling the first passage, operatively connected to the upper face of the piston and having exposed to pressure in said first passage an upper face having a diameter smaller than the diameter of the piston, a second valve member to control said second passage operatively connected to the piston and movable to a position closing the second passage, resilient means to bias the piston upwardly to maintain the first valve member closed until a predetermined gas pressure is exerted on the upper face of the first valve member to initiate the downward movement of the piston and expose the piston to the gas pressure to accelerate the downward movement of the piston and the closure of the second valve member and prevent the return of the piston upwardly to close the first valve member until the gas pressure drops substantially below said predetermined pressure in order to supply gas under pressure to said ram to advance it and to provide for exhausting gas back through the first and third passage to the accumulating chamber on the retraction of the ram, means to connect said accumulating chamber to the atmosphere to exhaust gas therefrom as the ram retracts, and a normally closed manually controlled valve in said second passage upstream of said second valve member controlling the second passage.

9. A device in accordance with claim 8 in which a fourth passage connects the accumulating chamber to the atmosphere and a normally open manually controlled valve in the fourth passage, said last mentioned manually controlled valve being connected to the first mentioned manually controlled valve.

* * * * *

UNITED STATES PATENT OFFICE
CERTIFICATE OF CORRECTION

Patent No. 3,945,379   Dated March 23, 1976

Inventor(s) Howard B. Pritz and Sherwood G. Talbert

It is certified that error appears in the above-identified patent and that said Letters Patent are hereby corrected as shown below:

In column 7, line 63, (claim 1), "prssure" should read "pressure". In column 8, line 25, (claim 2), "respeonsive" should read "responsive"; line 63, (claim 8), insert - - a - - before "third".

Signed and Sealed this

Twentieth Day of July 1976

[SEAL]

Attest:

RUTH C. MASON
Attesting Officer

C. MARSHALL DANN
Commissioner of Patents and Trademarks